United States Patent [19]
Johnson et al.

[11] Patent Number: 6,050,963
[45] Date of Patent: Apr. 18, 2000

[54] SYSTEM FOR ANALYZING THE MOTION OF LIFTING AN OBJECT

[75] Inventors: Lee Edward Johnson, Chicago; Steven Alan Lavender, Deerfield, both of Ill.

[73] Assignee: Innovative Sports Training, Inc., Chicago, Ill.

[21] Appl. No.: 09/099,100

[22] Filed: Jun. 18, 1998

[51] Int. Cl.$^7$ ................................................. A61B 5/103
[52] U.S. Cl. ........................................... 600/595; 600/587
[58] Field of Search ................................... 600/587, 594, 600/595

[56] References Cited

U.S. PATENT DOCUMENTS

| | | | |
|---|---|---|---|
| 3,820,130 | 6/1974 | Cornelison, Jr. et al. | 354/34 |
| 4,163,941 | 8/1979 | Linn, Jr. | 324/178 |
| 4,251,077 | 2/1981 | Pelz et al. | 273/186 |
| 4,304,406 | 12/1981 | Cromarty | 273/186 R |
| 4,451,043 | 5/1984 | Ogawa et al. | 273/186 R |
| 4,462,252 | 7/1984 | Smidt et al. | 73/379 |
| 4,524,348 | 6/1985 | Lefkowitz | 340/365 R |
| 4,631,676 | 12/1986 | Pugh | 364/413 |
| 4,655,227 | 4/1987 | Gracovetsky | 128/781 |
| 4,688,037 | 8/1987 | Krieg | 340/825.72 |
| 4,713,686 | 12/1987 | Ozaki et al. | 358/107 |
| 4,839,838 | 6/1989 | LaBiche et al. | 364/709.11 |
| 4,849,692 | 7/1989 | Blood | 324/208 |
| 4,869,509 | 9/1989 | Lee | 273/183 B |
| 4,891,748 | 1/1990 | Mann | 364/410 |
| 4,896,283 | 1/1990 | Hunt et al. | 364/577 |
| 4,911,441 | 3/1990 | Brunner | 273/29 A |
| 4,912,638 | 3/1990 | Pratt, Jr. | 600/595 |
| 4,938,476 | 7/1990 | Brunelle et al. | 600/595 |
| 4,951,079 | 8/1990 | Hoshino et al. | 354/412 |
| 4,979,745 | 12/1990 | Kobayashi | 273/186 R |
| 4,991,850 | 2/1991 | Wilhelm | 273/186 A |
| 5,034,811 | 7/1991 | Palm | 358/105 |
| 5,067,717 | 11/1991 | Harlan et al. | 273/186 A |
| 5,087,047 | 2/1992 | McConnell | 273/183 B |
| 5,111,410 | 5/1992 | Nakayama et al. | 364/551.01 |
| 5,143,088 | 9/1992 | Marras et al. | 600/594 |
| 5,154,427 | 10/1992 | Harlan et al. | 273/186.3 |
| 5,233,544 | 8/1993 | Kobayashi | 364/566 |
| 5,246,232 | 9/1993 | Eccher et al. | 364/559 |
| 5,269,318 | 12/1993 | Nashner | 600/595 |
| 5,297,061 | 3/1994 | Dementhon et al. | 273/184 R |
| 5,406,307 | 4/1995 | Hirayama et al. | 345/120 |
| 5,469,861 | 11/1995 | Piscopo et al. | 600/594 |
| 5,474,083 | 12/1995 | Church et al. | 600/595 |
| 5,511,789 | 4/1996 | Nakamura | 473/202 |
| 5,625,577 | 4/1997 | Kunii et al. | 364/578 |
| 5,638,300 | 6/1997 | Johnson | 364/551.01 |
| 5,672,815 | 9/1997 | Prutu | 73/65.07 |

FOREIGN PATENT DOCUMENTS

| | | |
|---|---|---|
| 0 278 150 | 8/1988 | European Pat. Off. |
| WO 91/06348 | 5/1991 | WIPO |

OTHER PUBLICATIONS

"Wavi™" advertisement. Published by Sports Technology, Inc., Essex, Connecticut.

"Sportech™" advertisement. Published by Sports Technology, Inc., Essex, Connecticut.

"Golftek" advertisement. Published by GolfTek, Lewiston, Idaho. Published 1992.

"Biovision™" advertisement. Published by the Optimum Human Performance Center, Menlo Park, California.

"Introducing the Swing Motion Trainer," by SportSense, Inc. Published by SportSense, Inc., Mountain View, California.

(List continued on next page.)

*Primary Examiner*—Cary O'Connor
*Assistant Examiner*—Charles Marmor, II
*Attorney, Agent, or Firm*—Brinks, Hofer, Gilson & Lione

[57] ABSTRACT

A method of analyzing the motion of an individual moving an object from a first position to a second position by calculating the moment of a first portion of an individual and producing a sensory signal that is representative of the magnitude of the calculated moment.

71 Claims, 4 Drawing Sheets

OTHER PUBLICATIONS

"SportSense" advertisement. Published by SportSense, Inc., Mountain View, California.

"Mythbuster—Breakthrough Technology Refutes Things about the Swing the Golf world has Long Accepted as Fact," by Jonathan Abrahams. Golf Magazine, Nov., 1992, pp. 88–89.

"Widen the Gap," by Jim McLean. Golf Magazine, Dec., 1992, pp. 49–51.

"X Factor 2 Closing the Gap," by Jim McLean. Golf Magazine, Aug., 1993, pp. 29–31.

"The Flock of Birds™ Position and Orientation Measurement System Installation and Operation Guide." Published in 1994 by Ascension Technology Corporation, Burlington, Vermont.

News release entitled "Ascension's Long Range Flock Chosen for State-of-the-Art Performance Animation System Developed by Pacific Data Image (PDI)," released by Ascension Technology Corporation, Inc., Burlington, Vermont.

"The Influence of Dynamic Factors on Triaxial Net Muscular Moments at the L5/S1 Joint During Asymmetrical Lifting and lowering," by Denis Gagnon, Biomechanics, vol. 25, No. 4, 1992, pp. 891–901.

"The Role of Dynamic Three–Dimensional Trunk Motion in Occupationally–Related Low Back Disorders—The Effects of Workplace Factors, Trunk Position, and Trunk Motion Characteristics on Risk of Injury," by William S. Marras et al., Spine, vol. 18, No. 5, pp. 617–628, 1993.

"Occupational Biomechanics—Second Edition," by Don B. Chaffin et al., published by Wiley–Interscience Publication/ John Wiley & Sons, Inc., 1991, pp. 202–239.

U.S. application No. 08/871,438, Johnson, filed Jun. 9, 1997, entitled "Golf Swing Analysis System" by Lee E. Johnson.

SYSTEM FOR ANALYZING THE MOTION OF LIFTING AN OBJECT

BACKGROUND OF THE INVENTION

1. Field of the Invention

The present invention relates to a system for analyzing the movement of an individual while lifting an object.

2. Discussion of Related Art

The back injury problem in the United States is significant, with some estimates of related costs being as high as $40 billion dollars. The scientific literature has shown that back injuries are due in large measure to the compressive forces generated on the spine. These compressive forces, in turn, are directly affected by the external moments and forces generated during lifting activities. The external moments that affect a joint result from the position and motion of the object being lifted and the position and motion of body segments that are attached to the joint.

Existing techniques used to educate workers in good lifting practice range from lectures and demonstrations to the use of devices that measure trunk angles and angular velocities. However, the training techniques do not compute joint moments acting on the spine as loads are lifted and so the individual is unable to determine whether the technique is properly reducing the joint moments.

SUMMARY OF THE INVENTION

A first aspect of the present invention concerns a motion analysis system for analyzing the motion of an individual moving an object from a first position to a second position. The motion analysis system includes a first sensor attached to a first portion of an individual for detecting the position and orientation of the first portion of the individual and producing a signal representative of the position and orientation. An analyzer receives the signal from the first sensor, wherein the analyzer calculates a moment of the first portion of the individual based upon the received signal. An indicating mechanism produces a sensory signal that is representative of the magnitude of the calculated moment.

A second aspect of the present invention regards a motion analysis system for analyzing the motion of an individual moving an object from a first position to a second position. A first sensor is attached to a first portion of an individual for detecting the position and orientation of the first portion of the individual and producing a signal representative of the position and orientation. A scale generates a weight signal representative of the weight of an object being moved from a first position to a second position and an analyzer is electronically connected to the first sensor and the scale, the analyzer calculates the center of mass of the object based on the first signal and the weight signal.

A third aspect of the present invention regards a method of analyzing the motion of an individual moving an object from a first position to a second position by calculating the moment of a first portion of an individual and producing a sensory signal that is representative of the magnitude of the calculated moment.

A fourth aspect of the present invention regards a method for analyzing the motion of an individual moving an object from a first position to a second position by moving an object from a first position to a second position; weighing the object during the moving step and calculating the moment of the object based on the weighing step.

A fifth aspect of the present invention regards a method for analyzing the motion of an individual moving an object from a first position to a second position by moving an object from a first position to a second position and measuring the force exerted by the object on an individual during the moving step and measuring a moment of a portion of the individual using a "top-down" methodology during the moving step.

Each aspect of the present invention provides the advantage of computing the joint moments while lifting an object and providing an individual with immediate feedback on the size of the moments being generated during various lifting activities to enable the individual to modify his or her lifting behavior in order to reduce the size of the moments generated on the spine and thereby reduce the likelihood of injury.

The foregoing features and advantages of the present invention will be further understood upon consideration of the following detailed description of the invention taken in conjunction with the accompanying drawings, in which:

DESCRIPTION OF THE PREFERRED EMBODIMENT

The motion analysis system of the present invention is best understood by a review of FIGS. 1–7. The description to follow will concern a motion system for analyzing the motion of lifting or moving an object from one position to another position. However, it is understood that the present invention can be used to analyze other motions of other objects held and moved by an individual.

Figure 1:
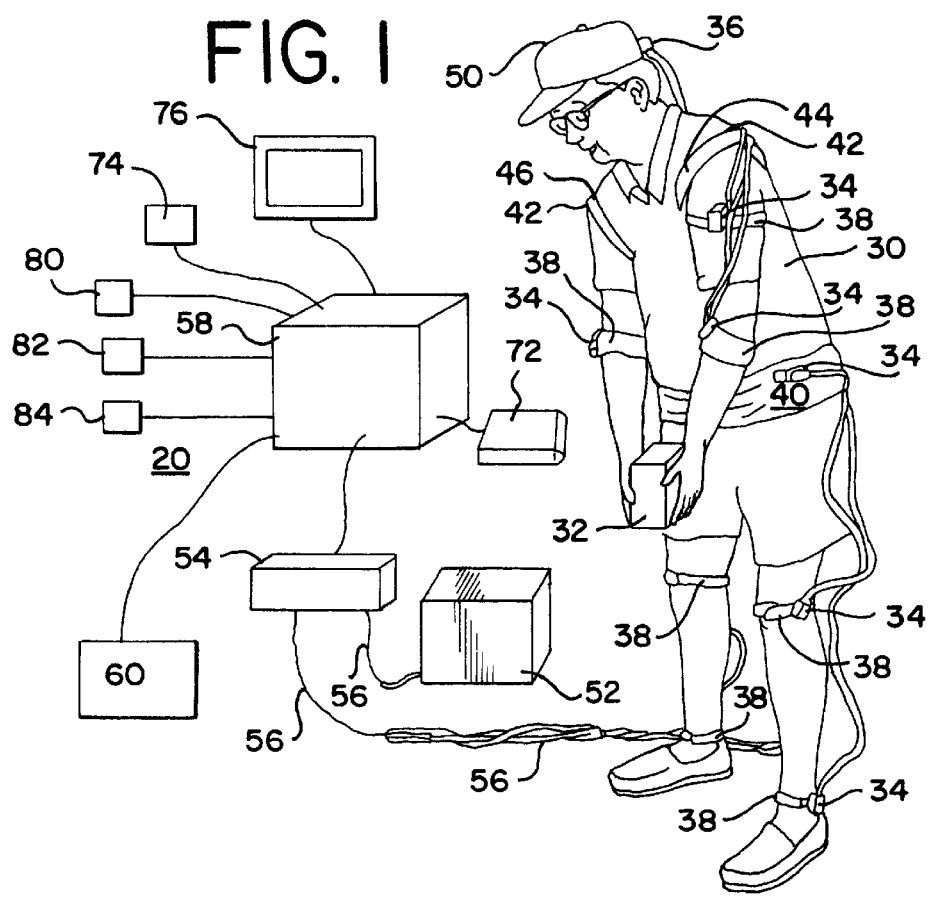
FIG. 1 shows a side view of an individual using the motion analysis system according to the present invention.
Figure 2:
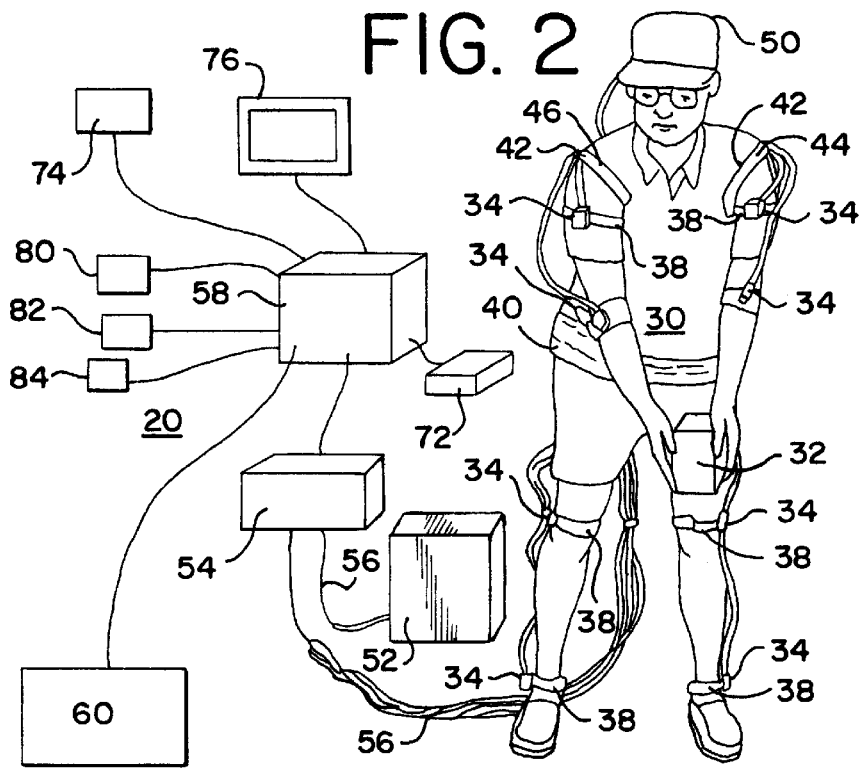
FIG. 2 shows a front view of an individual using the motion analysis system of FIG. 1.
Figure 3:
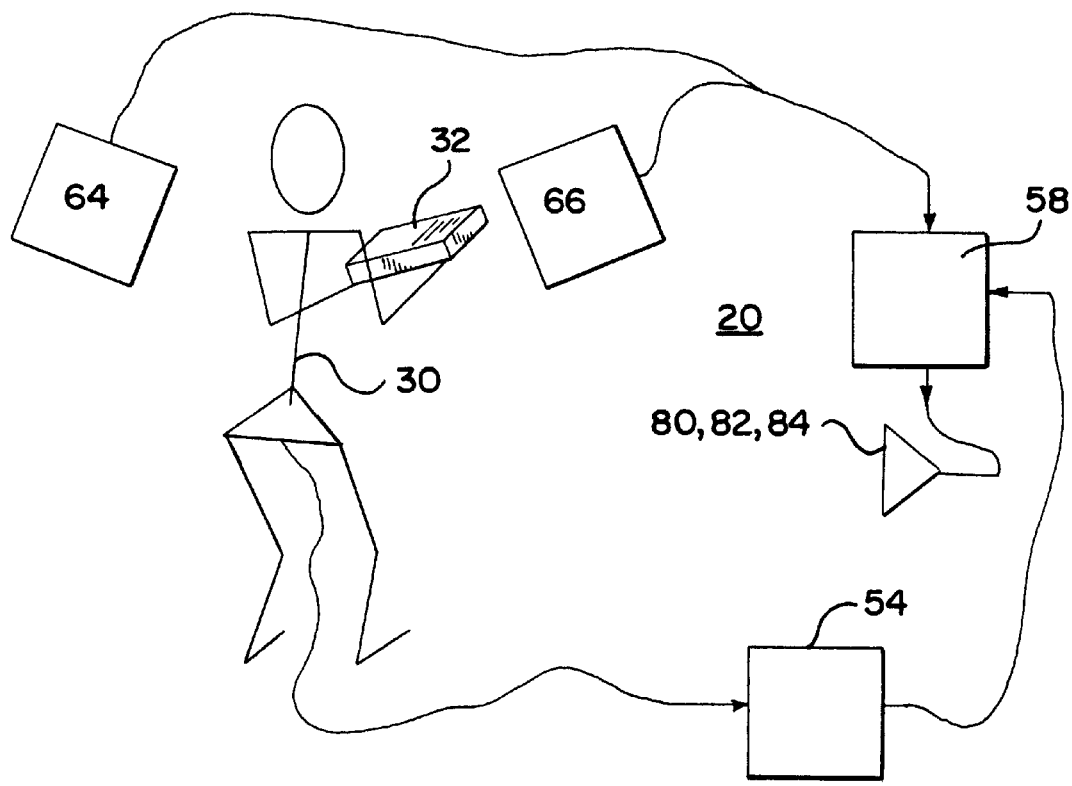
FIG. 3 schematically shows an individual moving an object while having his or her motion analyzed by the motion analysis system of FIGS. 1 and 2.

In FIGS. 1 and 2, a motion analysis system 20 is shown where an individual 30 is shown prior to his lifting of an object 32. A plurality of sensors 34 are positioned at several areas on the individual's body, such as the pelvis, torso, legs, thighs, forearms and upper arms, in order to thoroughly measure and analyze the motion of the individual 30 as he lifts the object 32. In particular, the sensors 34 are preferably placed on each body segment whose motion is to be tracked, wherein a body segment is defined to be a part of a body located between two joints of the body. It is understood that other sensors may be worn as well, such as on the hands or feet. A single sensor 36 for the individual's head is used as well. The sensors 34 for the legs, thighs, forearms and upper arms are preferably attached to straps 38 wrapped around the segment. The sensor 34 for the pelvis is attached to a belt 40 that is wrapped around the waist of the individual 30. The sensor 34 for the torso is attached to a shoulder harness 42.

Figure 4:
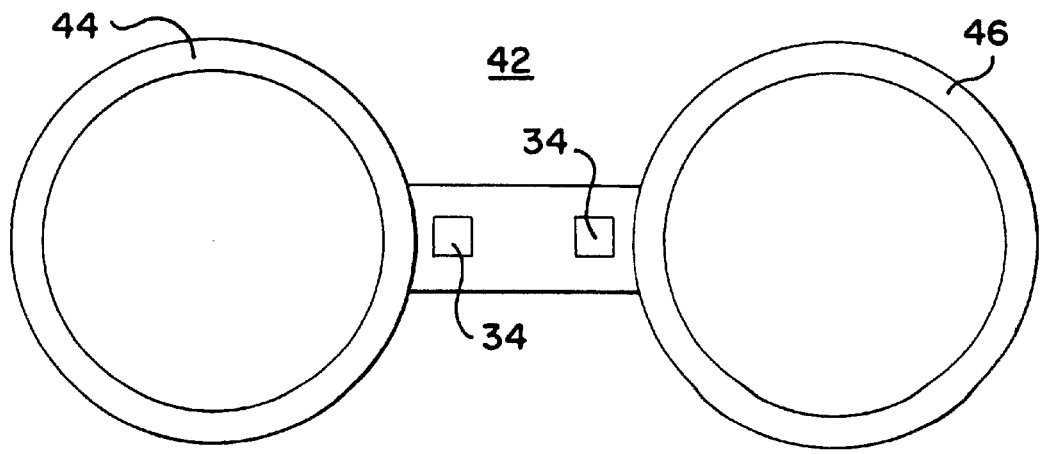
FIG. 4 shows a top view of a shoulder harness to be used with the motion analysis system of FIGS. 1–2.

As shown in FIG. 4, the shoulder harness 42 has a pair of loops 44, 46 that are joined together by a central support area 48 to which the torso sensor 34 is attached. As shown in FIGS. 1 and 2, the individual 30 places his arms through the loops 44 and 46 so that the central support area 48 and the torso sensor 34 is positioned at the C7/T1 spinal joint The sensors 34 are attached to the straps 38, the belt 40 and the central support area 48 by an adhesive or via a hook and loop attachment system, such as the system known by the name of VELCRO™. The sensor 36 for the head is attached to the back of a hat 50 by a hook and loop attachment system, such as the system known as VELCRO™. Since the hat 50, when worn, moves with the head of the individual, the sensor 36 attached thereto accurately detects head movement of the individual 30.

When sensors 34 and 36 are properly attached they form a sensor array that can be used to accurately track the motion of the individual 30 as he performs a typical motion, such as lifting the object 32. Preferably, the sensors 34 and 36 are used in conjunction with a radiation source 52 and a system control unit 54 so as to detect electromagnetic radiation emitted from radiation source 52 and generate signals representative of the position and orientation of the sensors 34 and 36 in a manner similar to that described in U.S. Pat. No. 5,638,300, whose entire contents are incorporated herein by reference.

As described in U.S. Pat. No. 5,638,300, the radiation source 52 preferably emits magnetic fields along three mutually orthogonal axes which are then detected by six degrees of freedom sensors 34 and 36. Upon detecting the magnetic fields, these sensors 34 and 36 are capable of producing signals representative of their position and orientation in space. These positions in space can be represented by such well known coordinate systems, such as x,y,z Cartesian coordinates, cylindrical coordinates, spherical coordinates and euler angles. Such a magnetic source and detector system is marketed under the name of The Flock of Birds™ made by Ascension Technology Corporation of Burlington, Vt. Ascension Technology Corporation is also the assignee of a magnetic source and detector patent—U.S. Pat. No. 4,849,692, whose entire contents are incorporated herein by reference.

The signals generated by sensors 34 and 36 are sent by wires 56 to the system control unit 54 which (i) converts the signals to readings indicative of each sensor's position and orientation and (ii) sends such readings to an analyzer, such as the computer 58. Other ways for sending the signals to system control unit 54 are also possible, such as radiofrequency (RF) transmissions sent by a transmitter in each sensor 34, 36 to a radio receiver connected to the computer 58.

The signals received by the system control unit 54 are then processed by the computer 58 to generate a number of parameters associated with the motion. For example, in those instances where the sensors 34 are not placed at an end point of a body segment, the computer 58 computes the positions of the end points from vectors computed during the calibration step described below that relate the position of the segment sensor to the end points of the segment. Thus, instead of placing a sensor 34 at each end point (eg., wrist and elbow) of a body segment (eg., forearm), a single sensor 34 is placed on the body segment and vectors are used to locate the positions of the two end points.

In the case of lifting or moving an object from one position to another, it is useful for the computer 58 to measure the forces and the moment experienced by a portion of the individual 30, such as the L5/S1 spinal joint of the individual 30. Note that the term moment as used previously and hereinafter is meant to mean the vectorial torque ($\tau = r \times F$) that is exerted on a particular joint of interest. The measured moment includes the effect of static forces, like gravity, acting on the object and body segments attached to the joint of interest as well as the dynamic forces created by the acceleration of the object and body segment. In order to measure the moment and the forces exerted on the L5/S1 spinal joint, it is first necessary to measure the weight of the object 32 exerted on the L5/S1 spinal joint. This is done by a weight measurement system 60 that is electrically connected to the computer 58 and sends signals to the computer 58 that is representative of the weight force exerted on the individual 30 by the object 32 during movement of the object 32.

Figure 5:
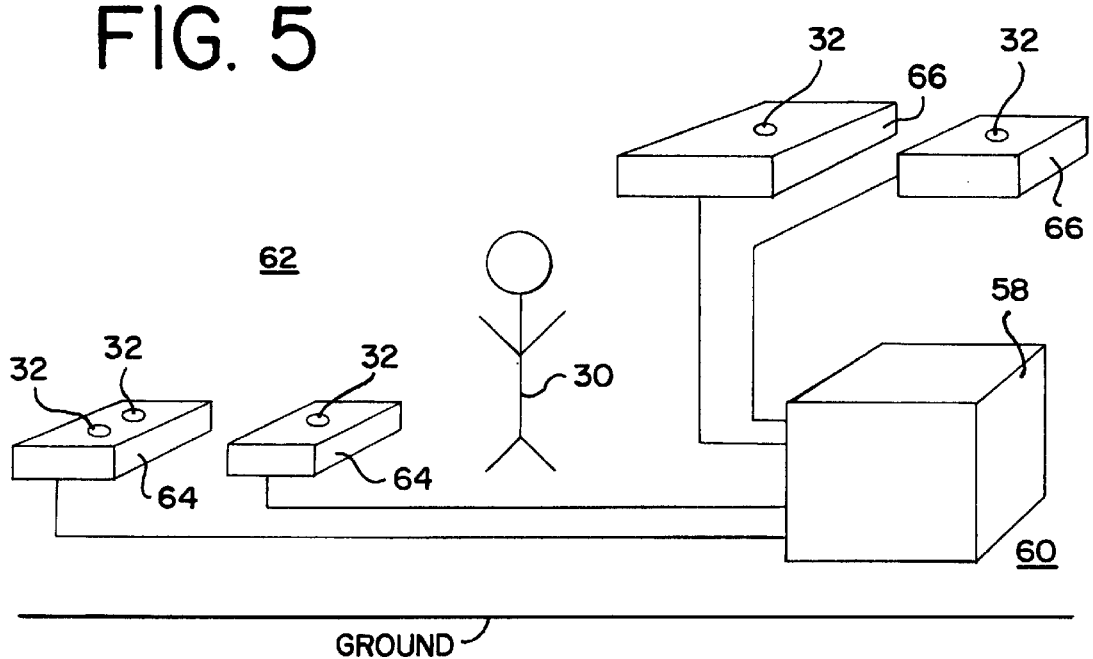
FIG. 5 schematically shows a scalar measurement system to be used with the motion analysis system of FIGS. 1–2.
Figure 6:
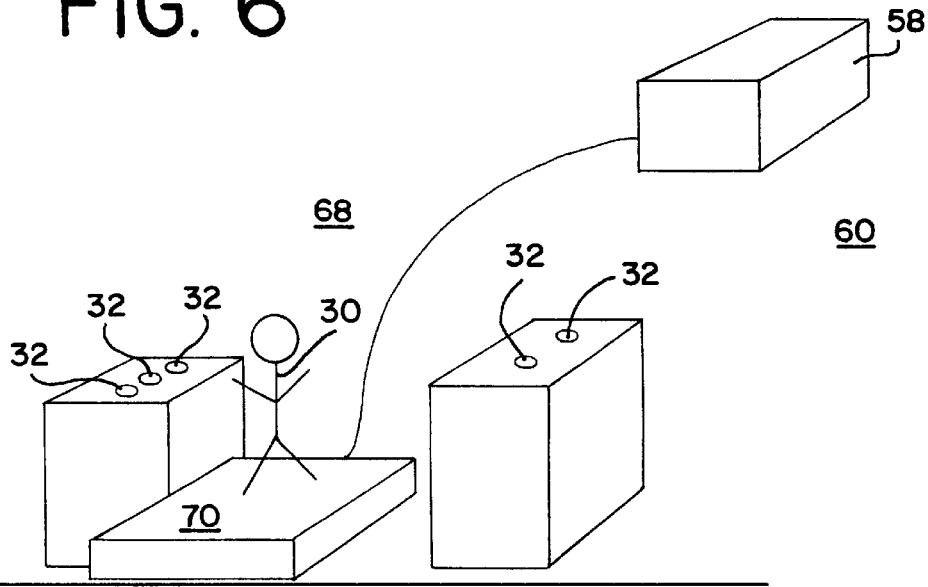
FIG. 6 schematically shows a vectorial measurement system to be used with the motion analysis system of FIGS. 1–2.

As shown in FIGS. 5–6, the weight measurement system 60 can be embodied as either a scalar weight measurement system or a vectorial weight measurement system. An example of a scalar weight measurement system 62 is shown in FIG. 5. This type of weight measurement system is typically used for analyzing motions performed that are similar to when an individual moves an object from a dispensing pallet located at one position to a receiving pallet located at another position. To simulate this motion, one or more dispensing scalar scales 64 that are well known in the art are positioned at the same height as the dispensing pallets would be positioned in real life. Similarly, one or more receiving scalar scales 66 are positioned at the same height and distance from the dispensing scalar scales 64 as the real life dispensing and receiving pallets are positioned relative to one another. Each of the scalar scales 64 and 66 are electronically connected to the computer 58 and send a signal representative of the scalar weight of the object(s) 32 that are positioned thereon. With all of the objects 32 on the dispensing scalar scales 64, the individual 30, while wearing the sensors 34 and 36, moves the objects 32 to the receiving scalar scales 66. Besides monitoring the positions of the sensors 34 and 36 during the movement of the objects 32, the computer 58 receives weight signals from the scales 64 and 66 that represent the total weight of the objects 32 measured by the scales 64 and 66 from the time before the movement of the objects 32 begins to the time that the movement is concluded. The computer 58 subtracts the total measured weight of the objects 32 during the movement from the weight of the objects 32 as measured prior to the movement. At any given moment, the subtracted difference is taken to be the weight of the object 32 being handled and moved by the individual 30 at that time.

A vectorial weight measurement system 68 is shown in FIG. 6. This type of weight measurement system may be used if the individual 30 typically stands in place when moving an object 32 from one place to another. In this case, the individual 30 stands on a ground reaction force device, such as a force plate 70 or an in-shoe force measurement system, that measures the magnitude and direction of the ground reaction forces that are generated by the body and the object 32 as it is being moved. The force plate 70 is electronically connected to the computer 58 and sends a signal representative of the ground reaction force (magnitude and direction) generated by the force plate 70.

With the above description in mind, the overall operation of the motion analysis system 20 will be described. In particular, the first step in operating the motion analysis system 20 is to calibrate the sensors 34 and 36 in a manner similar to that described in U.S. Pat. No. 5,638,300. Calibration is accomplished in a two step process. The first step involves the calculation of a vector offset that can be added to a segment sensor position to locate the segment endpoint. To accomplish this step, the location of each segment's endpoint is sequentially located by placing a sensor not attached to a body segment ("a measuring sensor") on each segment endpoint. As each endpoint is located, a simultaneous reading of the appropriate segment sensor is taken. The endpoint offset is then computed by taking the vector difference in the two readings. The second step in the calibration process involves the determination of a neutral or "zero" position for each sensor. This is accomplished by placing each sensor 34, 36 at a designated calibration position, holding the sensor at the designated calibration position for a predetermined amount of time, such as 1 second. The computer 58 then reads the signals from the sensor a pair of times. The signals are measured and compared with each other to see if they are within a predetermined tolerance level of each other, such as 0.25". Once the signals are within the tolerance level, the sensor is considered stable and so can be used. If the two signals are not within the tolerance level, the calibration process is repeated until the signals are within the tolerance level. After the sensors 34 and 36 have been calibrated, the motion of lifting an object can be analyzed.

Figure 7A:
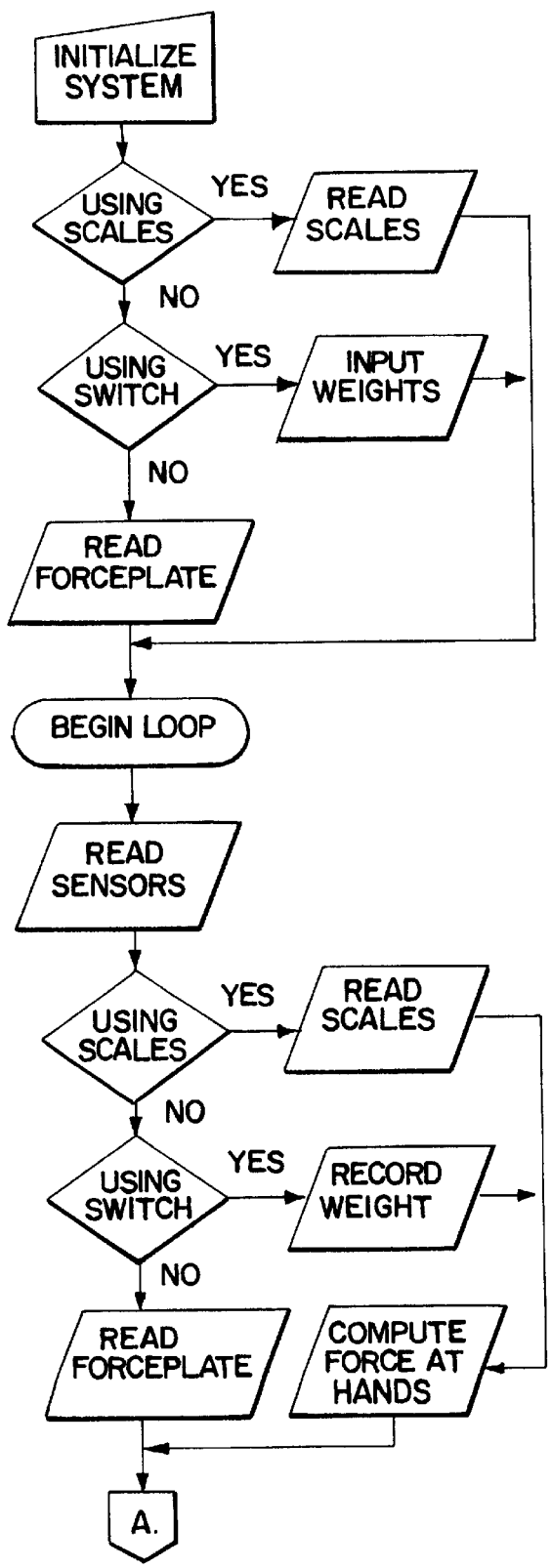
FIG. 7A shows a first portion of a general flow chart for operating the motion analysis system of FIG. 1.

As shown in FIG. 7A, the first step in operating the system system to initialize the system 20 by entering into the computer 58, via a keyboard 72, whether scalar scales 64, 66, a force plate 70 or a manual switch 74 is going to be used to determine the weight of the object 32 acting on the individual 30. Next, the variables of the system are initialized and the sensors 34 and 36 are attached to the body of the individual 30 in the manner described previously.

If the computer 58 is informed via the keyboard 72, that the scalar scales 64 and 66 are to be used, then the computer 58 receives weight signals from the scales 64 and 66 that are representative of the measured weights of the objects 32 on each of the scales 64 and 66 and sums all of the weight signals to give the total weight of the objects 32. The computer 58, via display 76, informs the individual 30 to stand on one of the scales 64 and 66. The scales 64 and 66 send a weight signal representative of the combined weight of the objects 32 and the individual 30. The computer 58 subtracts the weight of the objects 32 on the scale from the total combined weight on the scale so as to obtain the weight of the individual 30.

If the computer 58 is informed that a manual switch 78 is being used solely to indicate when the object 32 is being moved or lifted, then the weight of the object 32 and the individual 30 is input into the computer 58 via the keyboard 72. Note that using a switch 78 is a more economical way of determining when to begin and end a lifting session. In this technique, an observer presses the switch 78 to an on position to alert the motion analysis system 20 that he believes that the person has begun to lift the object. The observer presses the switch 78 to an off position when he believes that the person has completed his or her lift of the object. Pressing the switch 78 the second time signals the motion analysis system 20 that the lift is over. One drawback of this technique is that the times that the switch 78 is pressed may not accurately reflect the actual time that the lift began and/or ended.

If the computer 58 is informed that the force plate 70 is being used, then the display 76 requests the individual 30 to step onto the force plate 70. Once the individual 30 steps on the force plate 70, a signal is sent to the computer 58 that is representative of the magnitude and direction of the ground reaction force generated by the individual 30.

After the selection of either the scales 64, 66, manual switch 78 or the force plate 70, the motion analysis system 20 begins to measure the sensors 34, 36 and the selected weight measurement system every $1/100$ of a second. During each measurement, the sensors 34 and 36 are read and the computer 58 calculates the position of each sensor 34, 36 along with their linear velocity vector, angular velocity vector, linear acceleration vector and angular acceleration vector for each segment of the person's body that has a sensor 34, 36 attached thereto.

In those times where either the scales 64, 66 or the manual switch 78 are selected, the motion analysis system 20, besides reading the sensors 34 and 36, measures the position of the object 32 and the weight of the object 32 that the person encounters as he or she lifts and moves the object 32. The position of the object 32 and the weight of the object 32 encountered by the individual are two of the factors that are taken into account when calculating a moment of a joint of the individual. The measurement of the weight of the object 32 is performed during the same $1/100$ of a second sampling periods when the sensors 34 and 36 are read. If the individual initially indicates to the computer 58 that the scales 64 and 66 are to be used to measure the weight of the object 32, then prior to moving the object the total weight of all items, including the object, on the scales 64 and 66 is measured. After the object is initially moved, the total weight on the scales 64 and 66 is measured every $1/100$ of a second during the movement of the object. During the movement of the object, the measured total weight is then subtracted from the initial total weight measured in the initializing step every $1/100$ of a second, the difference being representative of the magnitude of the weight exerted on the hands of the individual 30 by the object 32. Once the magnitude of the weight of the object 32 being moved is known, it is possible to compute the reaction forces being generated on the hands due to the weight and acceleration of the object 32. The reaction force due to the weight of the object 32 is estimated to be equal in magnitude and opposite in direction to the gravitational force acting through the center of mass of the object 32. The computer 58 calculates the position of the center of mass of the object 32 based upon the calculated positions and orientations of the sensors 34 located on the forearms of the individual 30. The vector offsets computed in the calibration process described previously are added to the forearm sensor reading to locate the segment endpoints, in this case the wrists. In particular, the position of the center of mass of the lifted object 32 is estimated to be positioned midway between the positions of the left and right wrists. Knowing the position of the object at each time increment enables the calculation of the object's acceleration vector. With the weight of the object and its acceleration, the computer 58 calculates the reaction force that is due to the acceleration of the object as the product of the object's mass and its acceleration. Note that a more exact measurement of the center of mass of the object 32 can be accomplished by placing sensors 34 on the hands of the individual 30 and determining the center of mass to be midway between the sensors 34 on the hands.

If the manual switch 78 is being used and is in the on position, the computer 58 will record the weight being lifted and moved as the weight entered as described above for the process when scales 64, 66 are used. If the switch is in the off position, the analyzer will record a weight of zero since it believes that the object is no longer being lifted.

If a force plate 70 is used, then the force plate is read so as to generate a signal representative of the ground reaction force generated by the feet. As will be described below, the ground reaction force signal preferably is not used to weigh the lifted object alone or measure the position of the lifted object.

Figure 7B:
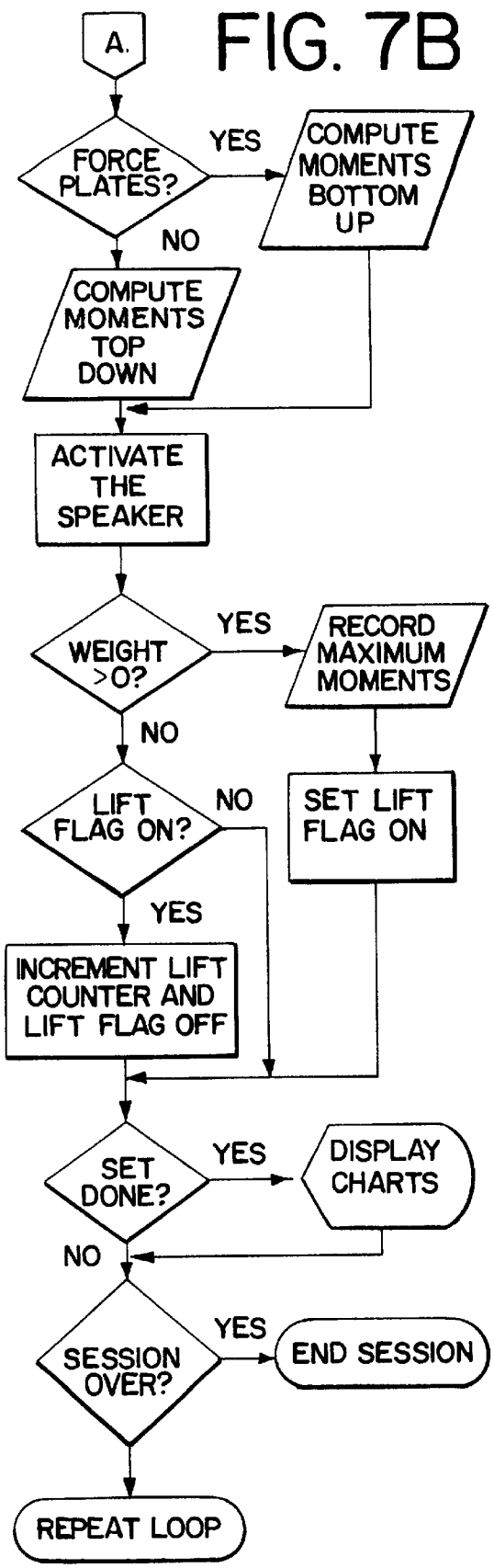
FIG. 7B shows a second portion of a general flow chart for operating the motion analysis system of FIG. 1.

As shown in FIG. 7B, the computer 58 calculates the moment of a portion of the individual like a joint of the individual, such as an elbow or the L5/S1 spinal joint, by processing the signals received from the sensors 34 and 36 and the calculated weight of the object 32 and/or the reaction forces at the feet or hands. In the cases where the weight of the object 32 is measured by either using the scales 64 and 66 or the manual switch 78, the moments and the forces exerted at each joint of the individual that has a sensor 34, 36 associated with it are calculated from the measured positions, and orientations, angular accelerations and angular velocities of the segments and the measured weight of the object 32 being moved from one position to another. As described in pages 202–239 of the second edition of the book entitled "Occupational Biomechanics," by Chafin and Andersson, the contents of which are incorporated herein by reference, it is a well known technique for the computer 58 to calculate the moment of a joint of the individual, such as an elbow or the L5/SI spinal joint, by the "top down" technique. This technique entails first determining the net reaction forces generated by the object 32 acting on the wrist joint. From the net reaction forces acting on the wrist joint and the mass, moment of inertia center of mass and the acceleration of the forearm segment, the net reaction force and moment acting on the elbow can be calculated. Similarly, the net reaction force and moment of the elbow and the mass, center of mass, moment of inertia and acceleration of the upper arm segment are used to calculate the net reaction force and moment acting on the shoulder joint. This process is repeated back to the segment of interest, like the L5/S1 spinal joint. Note that the mass, center of mass and moments of inertia for each segment can be estimated by well known regression equations.

If the force plate 70 is used to measure the reaction force encountered by the feet of the individual, then the computer 58 employs the well known "bottom up" technique for calculating the moment of a joint of the individual, such that the knee or the L5/S1 spinal joint of the individual 30. The "bottom-up" technique is explained in the article "The Influence of Dynamic Factors on Triaxial Net Muscular Movements at the L5/S1 Joint During Asymetrical Lifting and Lowering" by Gagnon and Gagnon and published at pages 891–901 of volume 25, no. 8 of Biomechanics, the entire contents of which are incorporated herein by reference. In this technique, the reaction force acting on the feet of the individual is known from the measurement from the force plate 70. If the reaction force on the feet is known and the mass, center of mass and moment of inertia of the feet are estimated as described above, then the reaction force and moments acting on the ankle joint can be calculated. With the calculated reaction forces and moments acting on the ankle joint, the reaction force and moments acting on the knee joint can be calculated from the measured positions, angular accelerations and angular velocities, the mass, center of mass and moment of inertia of the adjacent lower leg segment positioned between the ankle joint and the knee joint as measured by the motion analysis system 20. This process is continued until the reaction force and moments of the joint of interest is calculated. Accordingly, the "bottom up" technique allows the measured ground reaction force and the measured positions and orientations of the segments adjacent to the sensors 34 and 36 to be used to calculate the forces and moments at each joint, including the joint of interest, the knee or the L5/S1 spinal joint.

No matter which technique for measuring the weight of the object 32, the computer 58 calculates and measures the force exerted by the object 32 on the individual 30 and the moment of the joint of interest every $1/100$ of a second of the movement of the object 32 from one position to a second position. The computer 58 generates a signal proportional to the calculated moment of the joint of interest and sends the signal to an indicating mechanism, such as a light mechanism 80, a speaker mechanism 82 and/or a vibration mechanism 84, that produces a sensory signal that is representative of the magnitude of the calculated moment. In the case of the light mechanism 80, it preferably generates a light that varies in intensity and/or frequency/color that preferably is directly proportional to the magnitude of the calculated moment of the joint of interest. The indicating mechanism can also be a speaker mechanism 82 that generates a sound that varies in intensity/loudness and/or frequency that preferably is directly proportional to the magnitude of the calculated moment. A third embodiment for the indicating mechanism is a vibration mechanism 84 that generates a vibration that varies in intensity and/or frequency that preferably is directly proportional to the magnitude of the calculated moment. Of course, the light mechanism 80, the speaker mechanism 82, and the vibration mechanism 84 can be used in combination with one another.

With the above description of the motion analysis system 20 in mind, the system 20 can analyze the motion as an individual lifts an object in a manner similar to how it is performed in real life. Typical motions to be analyzed include the movement of an object from one pallet to another pallet or moving an object from a conveyor to another location. Prior to lifting the object, the sensors 34 and 36 are placed on the individual to be tested in the manner described previously. Next, the object(s) to be lifted are positioned at an initial position that is representative of the position that it would be in real life. For example, if the real life lifting motion to be simulated was to move one or more objects 32 from a pallet that is 2 feet above the ground to a pallet 6 feet above the ground, the objects 32 are initially placed 2 feet above the ground. In the case of using the scalar measurement system 62, the dispensing scales 64 would be placed above the ground so that when the objects 32 are placed thereon the objects are two feet above the ground. Similarly, the receiving scales 66 will be placed above the ground so that when the objects 32 are placed thereon the objects will be 6 feet above the ground.

Once the objects 32 are in their initial position, the individual 30 grabs one of the objects 32 with both hands and begins to move the object 32 so as to simulate a real life motion by moving the object 32 from the beginning position to a final position. As mentioned above, the motion analysis system 20 measures the positions of the sensors 34 and 36 and the weight of the object 32 that is exerted on the individual 30. Based on those measurements, the motion analysis system 20 calculates the location of the center of mass of the object and calculates the moment of a joint, such as the knee or the L5/S1 spinal joint, every $1/100$ of a second and produces a sensory signal, such as an audible tone, that can be sensed by an operator of the machine. In the case of the audible tone, the louder the tone becomes or the higher the frequency of the tone becomes is indicative that the moment of the joint is increasing. Similarly, a lowering in the loudness or frequency of the tone indicates a reduction in the moment of the joint. The ability to sense the audible tone allows the operator and the individual to identify portions of the simulated motion that cause undue stress on the joint.

Besides measuring the moment of the joint of the individual, the motion analysis system 20 is able to keep a record of the maximum moment calculated for the joint and the number of times objects are lifted during a session. As shown in FIG. 7A, the computer 58 registers when the weight of the object 32 exerted on the individual 30 first becomes non-zero. At that time, a flag is raised indicating that an object is being lifted. Furthermore, the computer 58 keeps track of the maximum moment measured during the lift. When the measured weight is equal to zero and the flag is raised, this indicates that a lift has been completed. At this stage, the flag is lowered and a counter is incremented by one indicating that one lift has been completed. When the flag is lowered, the display 76 generates a message to the operator asking whether other lifts are to be performed during the set. If the operator answers, via keyboard 72, in the negative, the process is repeated. If the answer is in the positive, the computer 58 produces a chart on the display that indicates the maximum moment measured at the joint of interest during each lift. Once the chart is displayed, the display 76 of the motion analysis system 20 will ask if other motion sets are to be analyzed or not.

Besides monitoring the moment of a joint, the motion analysis system can form a simulated moving picture, of the motion of the joints and the object 32 in a manner similar to that described in U.S. Pat. No. 5,638,300. In particular, a stick figure can be generated on the display 76 by having segments drawn based on the locations of the sensors 34 and 36. A facsimile of a humanoid can be generated as well in a well known manner.

Various options are possible with the simulated moving picture of a stick figure. For example, the simulated moving picture can be compared with a stored moving picture that represents an ideal lifting motion.

In addition, after viewing or comparing the simulated moving picture, the individual 30 may wish to play all of the frames of the motion and view it from several points of view, such as from the individual's front and back and above the individual 30. The above options of comparing moving pictures or viewing the simulated moving picture from various angles is described in U.S. Pat. No. 5,638,300, whose entire contents are incorporated herein by reference.

The foregoing description is provided to illustrate the invention, and is not to be construed as a limitation. Numerous additions, substitutions and other changes can be made to the invention without departing from its scope as set forth in the appended claims.

We claim:

1. A motion analysis system for analyzing the motion of an individual moving an object from a first position to a second position, said system comprising:
a first sensor attached to a first portion of an individual for detecting the position and orientation of said first portion of said individual and producing a signal representative of said position and orientation;
an analyzer for receiving said signal from said first sensor, wherein said analyzer calculates a moment of said first portion of said individual based upon said received signal; and
an indicating mechanism that produces a sensory signal that is representative of the magnitude of said calculated moment.

2. The motion analysis system of claim 1, wherein said indicating mechanism comprises a light mechanism that generates a light that varies in intensity depending on the magnitude of said calculated moment.

3. The motion analysis system of claim 2, wherein said intensity is directly proportional to said magnitude of said calculated moment.

4. The motion analysis system of claim 2, wherein said intensity is directly proportional to said magnitude of said calculated moment.

5. The motion analysis system of claim 1, wherein said indicating mechanism comprises a light mechanism that generates a light that varies in frequency depending on the magnitude of said calculated moment.

6. The motion analysis system of claim 5, wherein said frequency is directly proportional to said magnitude of said calculated moment.

7. The motion analysis system of claim 1, wherein said indicating mechanism comprises a speaker mechanism that generates a sound that varies in intensity depending on the magnitude of said calculated moment.

8. The motion analysis system of claim 1, wherein said indicating mechanism comprises a speaker mechanism that generates a sound that varies in frequency depending on the magnitude of said calculated moment.

9. The motion analysis system of claim 8, wherein said frequency is directly proportional to said magnitude of said calculated moment.

10. The motion analysis system of claim 1, wherein said indicating mechanism comprises a vibration mechanism that generates a vibration that varies in intensity depending on the magnitude of said calculated moment.

11. The motion analysis system of claim 10, wherein said intensity is directly proportional to said magnitude of said calculated moment.

12. The motion analysis system of claim 1, wherein said indicating mechanism comprises a vibration mechanism that generates a vibration that varies in frequency depending on the magnitude of said calculated moment.

13. The motion analysis system of claim 12, wherein said frequency is directly proportional to said magnitude of said calculated moment.

14. The motion analysis system of claim 1, wherein said first sensor is attached to said individual so as to be adjacent to a joint of said individual.

15. The motion analysis system of claim 14, wherein said joint comprises a knee of said individual.

16. The motion analysis system of claim 14, wherein said joint comprises a spinal joint of said individual.

17. The motion analysis system of claim 1, wherein said analyzer calculates said position and orientation of said first portion of said individual based upon said received signal.

18. The motion analysis system of claim 17, comprising a display that shows an image of said first portion of said individual based upon said calculated position of said first portion of said individual.

19. The motion analysis system of claim 1, wherein said first sensor comprises a six degrees of freedom sensor.

20. The motion analysis system of claim 1, further comprising:
a radiation source, wherein said first sensor receives radiation emitted from said radiation source to detect the position and orientation of said first portion of said individual.

21. The motion analysis system of claim 20, wherein said radiation source emits magnetic fields.

22. The motion analysis system of claim 20, wherein said radiation source comprises a radio-frequency transmitter that emits radio-frequency fields.

23. The motion analysis system of claim 1, wherein said analyzer takes into account the position of an object being moved from a first position to a second position when calculating said moment.

24. The motion analysis system of claim 23, wherein said analyzer takes into account the weight of said object when calculating said moment.

25. The motion analysis system of claim 23, further comprising:
a second sensor attached to a second portion of said individual that is located adjacent to said object, said second sensor produces a second signal representative of said position and orientation of said second portion of said individual;
wherein said analyzer receives said second signal from said second sensor, wherein said analyzer calculates the position and orientation of said second portion of said individual based upon said received signal from said second sensor.

26. The motion analysis system of claim 25, wherein said analyzer calculates the center of mass of said object based upon said calculated position of said second portion of said individual.

27. The motion analysis system of claim 26, further comprising:
a third sensor attached to a third portion of said individual that is located adjacent to said object, said third sensor produces a third signal representative of said position and orientation of said third portion of said individual;
wherein said analyzer receives said third signal from said third sensor, wherein said analyzer calculates the position and orientation of said third portion of said individual based upon said received signal from said third signal.

28. The motion analysis system of claim 27, wherein said analyzer calculates the center of mass of said object based upon said calculated positions of said second and third portions of said individual.

29. The motion analysis system of claim 28, wherein said center of mass of said object is calculated to be positioned midway between the calculated positions of said second and third portions of said individuals.

30. The motion analysis system of claim 29, wherein said second portion of said individual lies adjacent a hand of said individual that is used to move said object from said first position to said second position.

31. The motion analysis system of claim 30, wherein said third portion of said individual lies adjacent to the other hand of said individual that is used to move said object from said first position to said second position.

32. The motion analysis system of claim 1, wherein said analyzer takes into account the weight of said object when calculating said moment.

33. The motion analysis system of claim 32, further comprising a scale electrically connected to said analyzer, said scale generates and sends a weight signal to said analyzer that is representative of the weight of said object, said analyzer calculates said moment based on said weight signal.

34. The motion analysis system of claim 32, further comprising a scale electronically connected to said analyzer, said scale generates and sends to said analyzer (1) a first weight signal that is representative of the combined weight of one or more objects positioned on said scale including said object prior to moving said object from said first position to said second position and (2) a second weight signal representative of the combined weight of said one or more items positioned on said scale during said movement of said objects from said first position to said second position; and said analyzer takes the difference in the magnitudes of said first and second weight signals when taking into account the weight of said object when calculating said moment.

35. The motion analysis system of claim 1, comprising a manual switch that indicates when said object is initially moved from said first position and when said object is initially at said second position.

36. The motion analysis system of claim 35, comprising a manual switch that indicates when said object is initially moved from said first position and when said object is initially at said second position.

37. A motion analysis system for analyzing the motion of an individual moving an object from a first position to a second position, said system comprising:
a first sensor attached to a first portion of an individual for detecting the position and orientation of said first portion of said individual and producing a signal representative of said position and orientation;
a scale that generates a weight signal representative of the weight of an object being moved from a first position to a second position; and
an analyzer electronically connected to said first sensor and said scale, said analyzer calculates the center of mass of said object based on said signal representative of said position and orientation.

38. The motion analysis system of claim 37, further comprising:
a second sensor attached to a second portion of said individual that is located adjacent to said object, said second sensor produces a second signal representative of said position and orientation of said second portion of said individual;
said analyzer is electronically connected to said second sensor, said analyzer calculates the center of mass of said object based on said second signal.

39. The motion analysis system of claim 38, wherein said weight signal is representative of the combined weight of one or more objects positioned on said scale including said object prior to moving said object from said first position to said second position;
said scale generates a second weight signal representative of the combined weight of said one or more items positioned on said scale during said movement of said object from said first position to said second position;
said analyzer takes the difference in the magnitudes of said weight signal and said second weight signal into account when calculating the center of mass of said object; and
said analyzer takes the difference in the magnitudes of said first and second weight signals when taking into account the weight of said object when calculating said moment.

40. The motion analysis system of claim 38, wherein said center of mass of said object is calculated to be positioned midway between the calculated positions of said first and second portions of said individual.

41. The motion analysis system of claim 40, wherein said first portion of said individual lies adjacent a hand of said individual that is used to move said object from said first position to said second position.

42. The motion analysis system of claim 41, wherein said second portion of said individual lies adjacent to the other hand of said individual that is used to move said object from said first position to said second position.

43. The motion analysis system of claim 37, further comprising:

a second sensor attached to a second portion of an individual for detecting the position and orientation of said second portion of said individual and producing a signal representative of said position and orientation;

wherein said analyzer calculates a moment of said second portion of said individual based upon said first and second signals; and an indicating mechanism that produces a sensory signal that is representative of the magnitude of said calculated moment.

44. The motion analysis system of claim 43, wherein said calculated moment comprises the moment of said second portion of said individual.

45. The motion analysis system of claim 43, wherein said indicating mechanism comprises a light mechanism that generates a light that varies in intensity depending on the magnitude of said calculated moment.

46. The motion analysis system of claim 43, wherein said indicating mechanism comprises a light mechanism that generates a light that varies in frequency depending on the magnitude of said calculated moment.

47. The motion analysis system of claim 43, wherein said indicating mechanism comprises a speaker mechanism that generates a sound that varies in intensity depending on the magnitude of said calculated moment.

48. The motion analysis system of claim 43, wherein said indicating mechanism comprises a speaker mechanism that generates a sound that varies in frequency depending on the magnitude of said calculated moment.

49. The motion analysis system of claim 43, wherein said indicating mechanism comprises a vibration mechanism that generates a vibration that varies in intensity depending on the magnitude of said calculated moment.

50. The motion analysis system of claim 43, wherein said indicating mechanism comprises a vibration mechanism that generates a vibration that varies in frequency depending on the magnitude of said calculated moment.

51. A method of analyzing the motion of an individual moving an object from a first position to a second position, the method comprising the steps of:

calculating a moment of a first portion of an individual; and producing a sensory signal that is representative of the magnitude of said calculated moment.

52. The method of claim 51, comprising the step of detecting the position and orientation of said first portion of said individual prior to said calculating step.

53. The method of claim 51, wherein said producing step comprises varying the intensity of said sensory signal depending on the magnitude of said calculated moment.

54. The method of claim 51, wherein said producing step comprises varying the frequency of said sensory signal depending on the magnitude of said calculated moment.

55. The method of claim 51, wherein said first portion a joint of said individual.

56. The method of claim 55, wherein said joint comprises a spinal joint of said individual.

57. The method of claim 51, comprising the steps of:
said individual moving an object from a first position to a second position prior to said calculating step; and
wherein said calculating step takes into account the position of said object when calculating said moment.

58. The method of claim 51, comprising the steps of:
said individual moving an object from a first position to a second position prior to said calculating step; and
wherein said calculating step takes into account the weight of said object when calculating said moment.

59. The method of claim 51, comprising the steps of:
said individual grabbing an object with two hands; and
calculating the center of mass of said object.

60. The method of claim 59, wherein said step of calculating the center of mass comprises calculating the midway point between said two hands.

61. A method for analyzing the motion of an individual moving an object from a first position to a second position, the method comprising the steps of:

moving an object from a first position to a second position;

weighing said object during said moving step; and calculating the center of mass of said object based on said weighing step.

62. The method of claim 61, comprising the step of calculating the position of said object during said moving step;

wherein said step of calculating the center of mass is based on said calculated position.

63. The method of claim 62, comprising the steps of:
placing two hands on said object during said moving step;

calculating the positions of said two hands during said moving step; and wherein said step of calculating the center of mass takes into account said calculated positions of said two hands.

64. A method for analyzing the motion of an individual moving an object from a first position to a second position, the method comprising the steps of:

moving an object from a first position to a second position;

measuring the force exerted by said object on an individual during said moving step; and measuring a moment of a portion of said individual using a "top-down" methodology during said moving step.

65. The method of claim 64, wherein said measuring step comprises subtracting the reading on a scale as said object is being moved during said moving step with a reading on said scale that is made prior to said moving step.

66. The method of claim 65, comprising the step of:
producing a sensory signal that is representative of the magnitude of said calculated moment.

67. The method of claim 66, wherein said producing step comprises the step of varying the intensity of said sensory signal depending on the magnitude of said calculated moment.

68. The method of claim 66, wherein said producing step comprises the step of varying the frequency of said sensory signal depending on the magnitude of said calculated moment.

69. The method of claim 64, comprising the step of:
producing a sensory signal that is representative of the magnitude of said calculated moment.

70. The method of claim 69, wherein said producing step comprises the step of varying the intensity of said sensory signal depending on the magnitude of said calculated moment.

71. The method of claim 69, wherein said producing step comprises the step of varying the frequency of said sensory signal depending on the magnitude of said calculated moment.

* * * * *

UNITED STATES PATENT AND TRADEMARK OFFICE
CERTIFICATE OF CORRECTION

PATENT NO. : 6,050,963
DATED : April 18, 2000
INVENTOR(S) : Lee E. Johnson et al.

It is certified that error appears in the above-identified patent and that said Letters Patent is hereby corrected as shown below:

Claim 55,
Line 1, delete "portion a" and substitute -- portion comprises a -- in its place.

Signed and Sealed this

Ninth Day of October, 2001

Attest:

NICHOLAS P. GODICI
Attesting Officer
Acting Director of the United States Patent and Trademark Office